United States Patent
Holmes

(10) Patent No.: US 6,949,108 B2
(45) Date of Patent: Sep. 27, 2005

(54) CURETTE WITH DETACHABLE TIP

(75) Inventor: Russell P. Holmes, Boston, MA (US)

(73) Assignee: Hol-Med Corporation, South Easton, MA (US)

( * ) Notice: Subject to any disclaimer, the term of this patent is extended or adjusted under 35 U.S.C. 154(b) by 338 days.

(21) Appl. No.: 10/086,750

(22) Filed: Feb. 28, 2002

(65) Prior Publication Data

US 2002/0120283 A1 Aug. 29, 2002

Related U.S. Application Data

(60) Provisional application No. 60/272,173, filed on Feb. 28, 2001.

(51) Int. Cl.$^7$ .............................................. A61B 17/22
(52) U.S. Cl. ..................................................... 606/160
(58) Field of Search ............................... 606/160–162, 606/169; 15/106; 433/141

(56) References Cited

U.S. PATENT DOCUMENTS

| | | | | |
|---|---|---|---|---|
| 1,980,826 A | * | 11/1934 | Reiss | ........................ 606/161 |
| 4,777,947 A | * | 10/1988 | Zwick | ........................ 606/160 |
| 4,813,413 A | | 3/1989 | Gray | |
| 5,586,989 A | | 12/1996 | Bray, Jr. | |
| 5,863,260 A | * | 1/1999 | Butler et al. | ................ 473/305 |
| 6,196,936 B1 | * | 3/2001 | Meckel | ........................ 473/349 |
| 6,361,317 B1 | * | 3/2002 | Rahman | ...................... 433/141 |
| 6,391,040 B1 | * | 5/2002 | Christoudias | ................ 606/162 |
| 6,729,877 B2 | * | 5/2004 | Rahman | ...................... 433/141 |

* cited by examiner

*Primary Examiner*—(Jackie) Tan-Uyen T. Ho
(74) *Attorney, Agent, or Firm*—Cesari and McKenna, LLP

(57) ABSTRACT

The invention is a curette that includes a tip and shaft that detachably join together to form a working tool member. The shaft has a threaded receiving end that is sized to receive a mating end of the tip. The mating, or proximal, end of the tip includes a corresponding threaded section and a smaller-diameter outwardly extending elongated section that is flattened on one or more sides. To attach the tip to the shaft, a user partially fills the receiving end of the shaft with epoxy. The user then inserts the mating end of the tip into the receiving end of the shaft, such that the epoxy surrounds the elongated section of the mating end and fills or partially fills the threads. The user then screws the tip and shaft together, to interlock, or self-lock, the threads. When the epoxy thereafter hardens, the tip is firmly held against rotation relative to the shaft both by the epoxied and interlocked threads and the flattened-sided section that, because of its shape, resists rotation within the hardened epoxy. When the tip needs replacing, the tip is detached from the shaft by applying moderate heat to soften the epoxy and, thereafter, unscrewing the locking threads.

20 Claims, 5 Drawing Sheets

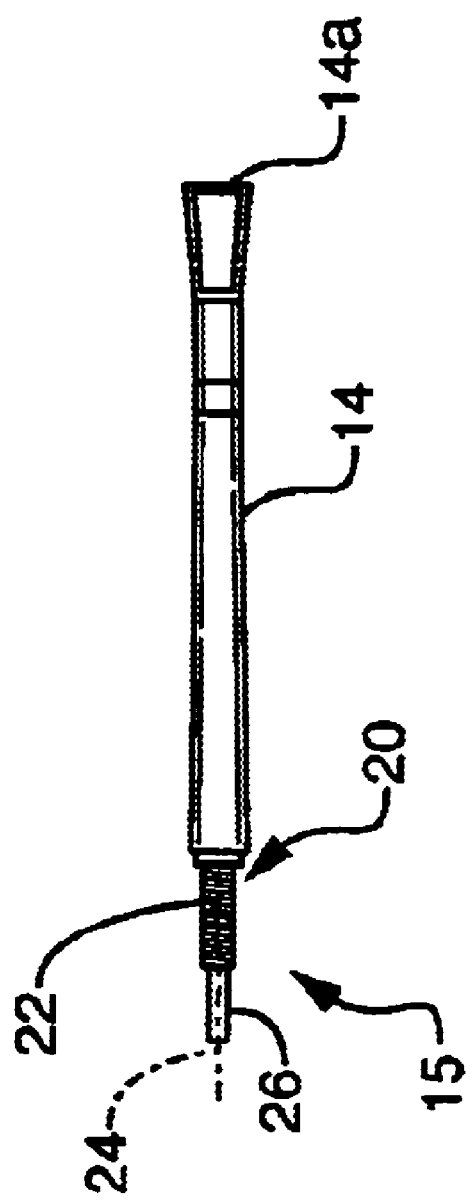

CURETTE WITH DETACHABLE TIP

CROSS-REFERENCE TO RELATED APPLICATIONS

The present application claims the benefit of U.S. Provisional patent application Ser. No. 60/272,173, which was filed on Feb. 28, 2001, by Russell P. Holmes for an IMPROVED CURETTE and is hereby incorporated by reference.

BACKGROUND OF THE INVENTION

1. Field of the Invention

The invention relates generally to curettes for use in surgical procedures.

2. Background Information

Curettes are used in surgical operations as scraping tools. The curette consists of a handle and a working tool member that includes an elongated shaft and a shaped tip, such as a scoop or ring. The tip has a sharpened edge that facilitates the scraping. For added durability, the working tool member may be coated with a durable coating, such as titanium nitrate.

The working tool member is generally constructed either as a one piece member or with the tip and shaft permanently welded together. The handle permanently or detachably joins to a proximal end of the member.

The one-piece and welded working tool members are relatively expensive to manufacture. Further, when the tip becomes worn, the entire member must be replaced, thus adding to the overall cost of the tool. Also, the welded tool member may be damaged by excess heat during welding, which results in a softening of the material of the shaft and/or the tip, and thus, reduces the useful life of the working tool member.

A coating of titanium nitrate may be added to the working tool member to strengthen the tip. With a one-piece or welded working tool member, part or all of the elongated shaft is also coated. If less than the entire member is to be coated, the manufacturer must cover the portions that are to remain uncoated, which add labor costs to the process. Whether or not the entire member is coated, the entire member must be baked, to cure the coating. Thus, relatively few pieces can be cured at a given time, making the coating process relatively expensive.

SUMMARY OF THE INVENTION

The invention is a curette that includes a tip and shaft that detachably join together to form a working tool member. The shaft has a threaded receiving end that is sized to receive a mating end of the tip. The mating, or proximal, end of the tip includes a corresponding threaded section and a smaller-diameter outwardly extending elongated section that is flattened on one or more sides. To attach the tip to the shaft, a user partially fills the receiving end of the shaft with epoxy. The user then inserts the mating end of the tip into the receiving end of the shaft, such that the epoxy surrounds the elongated section of the mating end and fills or partially fills the threads. The user then screws the tip and shaft together, to interlock, or self-lock, the threads. When the epoxy is thereafter hardens, the tip is firmly held against rotation relative to the shaft both by the epoxied and interlocked threads and the flattened-sided section that, because of its shape, resists rotation within the hardened epoxy.

When the tip needs replacing, the tip is detached from the shaft by applying moderate heat to soften the epoxy and, thereafter, unscrewing the locking threads. In contrast to welding, the temperature to which the epoxy must be heated for softening is sufficiently low that the heating does not soften the material of either the shaft or the tip.

The shaft and tip are relatively inexpensive to manufacture. Further, a titanium nitrate coating may be readily applied to only the tip before assembly of the tool member. The coating operation is thus relatively inexpensive to perform when compared to coating operations which coat the tip and all or a portion of the elongated shaft that is a permanent part of the one-piece or welded working tool member. Also, replacement costs are minimized with the current curette, because only the tip is replaced rather than an entire working tool member.

BRIEF DESCRIPTION OF THE DRAWINGS

FIG. 3 is a view of a tip that is part of a working tool member of FIG. 2;

DETAILED DESCRIPTION OF AN ILLUSTRATIVE EMBODIMENT

Figure 1A:
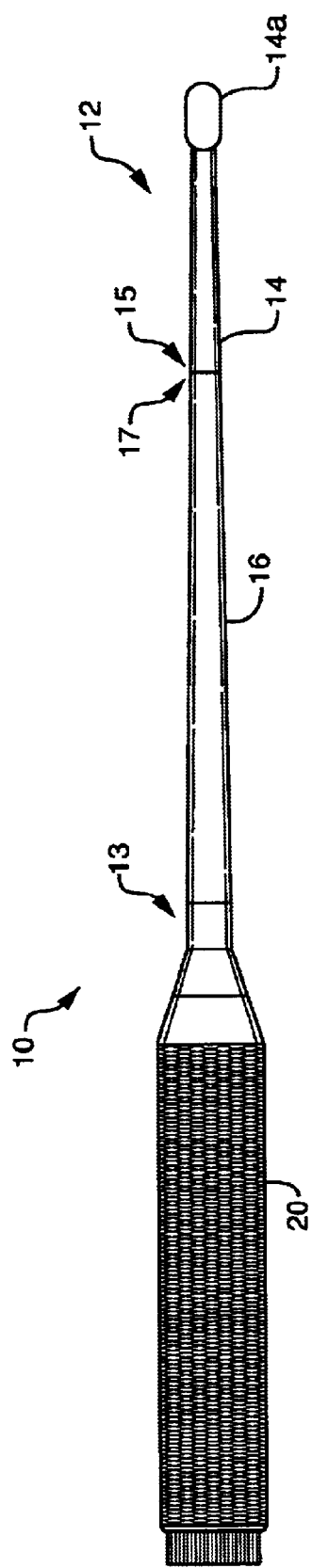
FIGS. 1A and 1B illustrate a curette that is constructed in accordance with the invention.
Figure 1B:
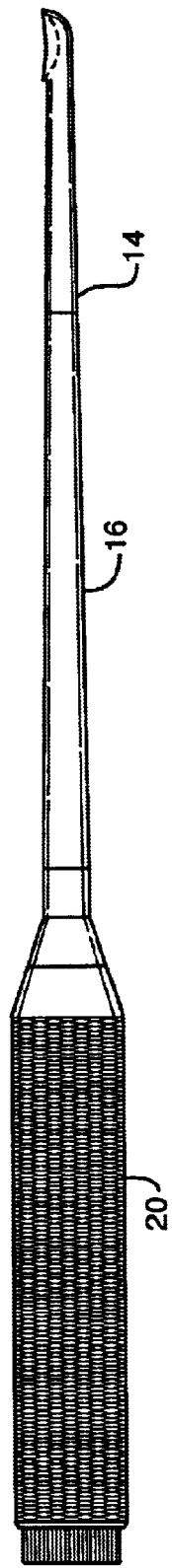
Figure 2:
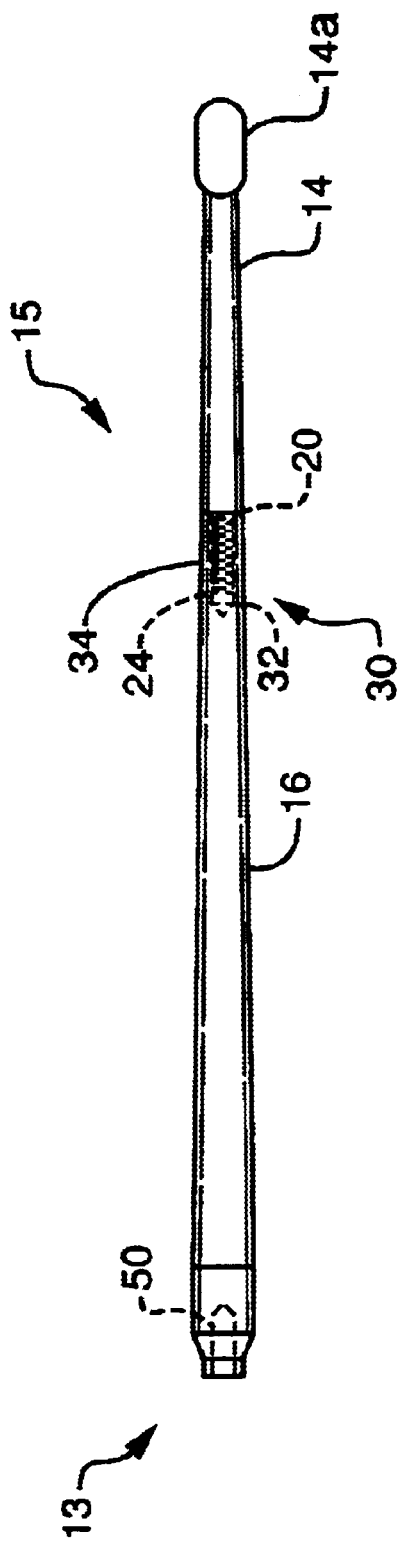
FIG. 2 is a cut-away view of a working tool member that is part of the curette of FIG. 1.

Referring to FIG. 1, a curette 10 includes a working tool member 12 that consists of a detachable tip 14 and a shaft 16. The tip 14 and shaft 16 connect together at mating ends 15 and 17, and a handle 20 detachably or permanently attaches to an opposite, or proximal, end 13 of the working tool member 12. The tip 14 may have a working end 14a that is shaped as a scoop, as shown in FIG. 2. Alternatively, the working end 14a may have various other shapes that are common to curettes, some of which are depicted in FIGS. 3 and 5.

Figure 4A:
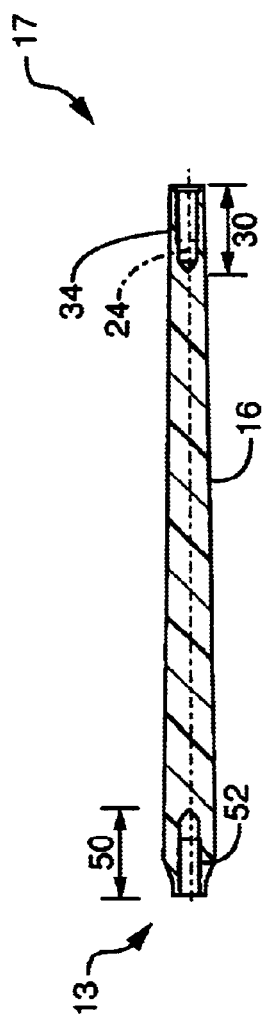
FIG. 4 is a cutaway view of a shaft that is part in the working tool member of FIG. 2.
Figure 4B:
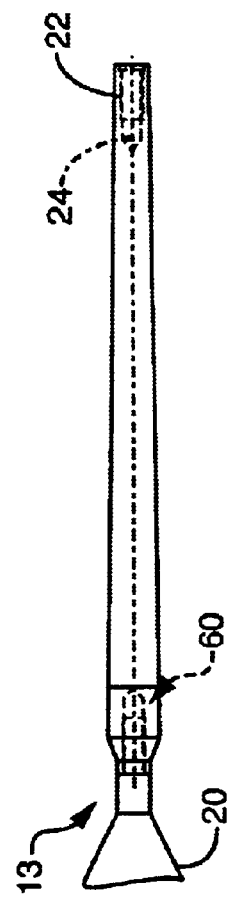
Figure 5:
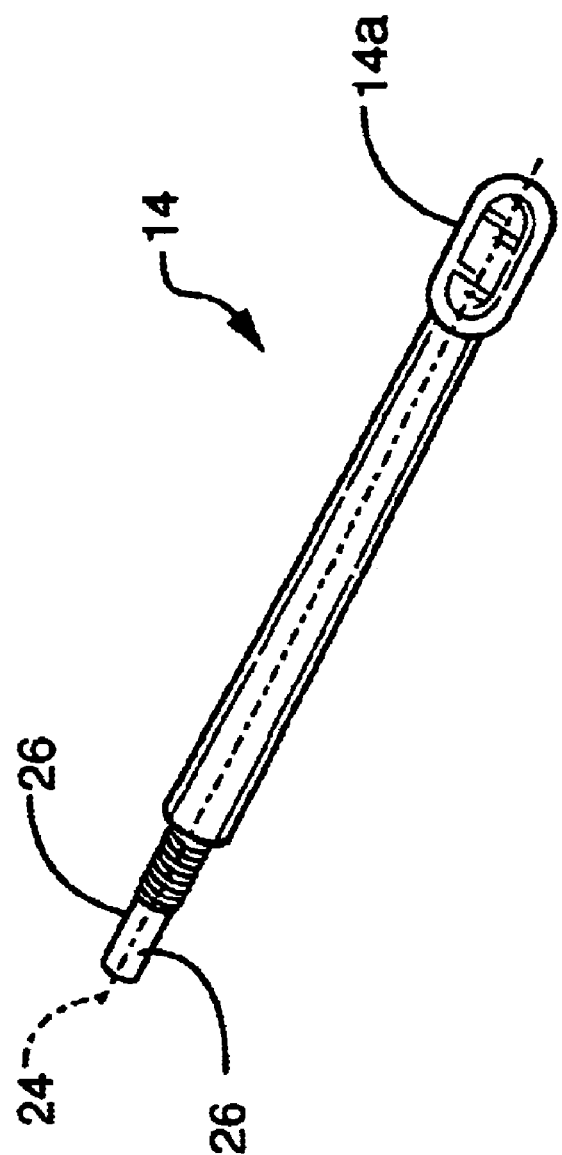
FIG. 5 is an angled view of the tip of FIG. 3.

Referring also to FIGS. 2–5, the mating end 15 of the tip 14 includes a threaded section 20 and an elongated end 24 that is flattened on at least one side 26. The elongated end may also may be flattened on additional sides 26, as depicted in FIG. 5. Preferably, there is a slight gap between the threads 22 and the start of the flattened portions 26 which extend to the outer end of the section 24. The mating, or distal, end 17 of the shaft 16 includes a receiving indent 30 that is shaped to receive the sections 20 and 24 of the mating end 15 of the tip 14. The indent 30 includes threads 32 that mate with and lock to the threads 22 of the threaded section 20 of the tip 14, when the mating ends are screwed together.

Before a user joins the tip 14 and shaft 16 together at their mating ends 15 and 17, the user partially fills the indent 30 with epoxy 34. Before the epoxy hardens, the user fits the mating, or proximal, end 15 of the tip 14 into the indent 30, such that the epoxy surrounds the elongated section 24 and fills or partially fills the threads 32 and/or 22. The user then screws the tip and shaft together to engage, or lock, the two sets of threads 22 and 32. When the epoxy 34 hardens, the epoxy holds the flattened side or sides 26 of the elongated end 24 against rotation. The epoxied interlocking threads and the epoxy-surrounded flattened-sided section together prevent the relative rotational movement of the tip and shaft when the curette is used during surgery. Indeed, the amount of torque that is required to loosen the interlocked threads once the epoxy hardens exceeds the amount of torque required to loosen the interlocked threads alone, and greatly exceeds the torque encountered during surgery.

When the tip 14 becomes worn, or dulled or otherwise requires replacement, the user heats the working tool member 12 at the connection between the tip 14 and the shaft 16, to soften the epoxy 34. The user then rotates the tip 14 relative to the shaft 16, or vice versa, in a direction that disengages, or unthreads, the threads 22 and 32. After the worn is tip 14 is removed from the shaft, another tip 14 may be attached in the same manner as discussed above.

The proximal end 13 of the shaft 16 detachably connects to the handle 20. The connection between the shaft 16 and the handle 20 may be made in the same manner as the connection between the tip 14 and the shaft 16. As depicted in FIG. 2, the shaft 16 includes an indent 50 that is shaped and threaded to receive a distal end 60 of the handle 20. The distal end 60, which is shown in phantom in FIG. 4B, is identical in shape to the proximal end 15 of the tip 14. The distal end 60 thus includes a threaded section 62 and a smaller-diameter outwardly extending section 64 with one or more flattened sides.

The connection between the shaft 16 and the handle 20 may instead be made in the manner discussed in U.S. Pat. No. 4,813,413 to Gray, which is incorporated herein by reference. Alternatively, the handle 20 may be permanently or detachably attached to the proximal end 13 of the shaft 16 in a conventional manner.

Prior to attachment to the shaft 16, the tip 14 may be coated in titanium nitrate from a working end 14a to the start of the threads 22. The tip is then baked to cure the coating. Given the small size of the tip, many more tips can be cured simultaneously in a given oven, when compared to the number of the larger one-piece or welded working tool members that can be simultaneously cured after coating. Accordingly, the cost of the coating operation is significantly reduced using just the tips. Replacement costs are also reduced, since the coated tip 14 can be readily replaced on the end of the re-usable shaft 16, which is in contrast to known prior curettes that require replacement of the entire working tool member.

What is claimed is:

1. A curette including:
    a detachable tip with a proximal mating end that includes a threaded section and an outwardly extending elongated section with one or more flattened sides;
    a shaft with a proximal end and a distal mating end, the distal end including a threaded indent for receiving the proximal mating end of the tip, the indent being sized to contain epoxy that hardens around the elongated section of the proximal mating end of the tip when the proximal end of the tip and the distal end of the shaft mate; and
    a handle with a distal end and a proximal end, the distal end being shaped to mate with the proximal end of the shaft.

2. The curette of claim 1 wherein the threads of the threaded sections of the tip and the shaft interlock when the proximal end of the tip and the distal end of the shaft mate.

3. The curette of claim 1 wherein
    the distal end of the handle includes a threaded section and an outwardly extending elongated section with one or more flattened sides, and
    the proximal end of the shaft includes a threaded indent that is shaped to receive the distal end of the handle, the indent being sized to contain epoxy that hardens around the elongated section of the distal end of the handle when the proximal end of the shaft and the distal end of the handle mate.

4. The curette of claim 2 wherein the tip has a distal end that is shaped for scraping.

5. The curette of claim 4 wherein the tip is coated with a durable coating from a proximal end to the threaded section.

6. The curette of claim 5 wherein the durable coating is titanium nitrate.

7. The curette of claim 4 wherein the distal end of the tip is shaped as one of a scoop or a ring.

8. A method for assembling a curette, the method including the steps of:
    partially filling a threaded indent in a distal end of a shaft with epoxy, the indent being shaped to receive a mating end of a tip;
    inserting the mating end of the tip in the partially-filled indent and screwing the shaft and tip together to interlock threads on the mating end of the tip with the threads in the indent, with the epoxy hardening around an elongated outwardly extending section of the mating end of the tip; and
    attaching a handle to a proximal end of the shaft.

9. The method of claim 8 wherein the step of attaching the handle includes inserting the distal end of the handle into a shaped indent in the proximal end of the shaft.

10. The method of claim 9 wherein the step of attaching the handle further includes partially filling the shaped indent in the proximal end of the shaft with epoxy, the epoxy surrounding an elongated outwardly extending portion of the distal end of the handle when the handle is attached to the shaft.

11. The method of claim 10 wherein the step of attaching further includes screwing together threads on the distal end of the handle and threads in the indent in the proximal end of the shaft until the threads interlock.

12. The method of claim 8 further including a step of removing a worn or dulled tip by heating the proximal end of the tip and the distal end of the shaft until the epoxy softens and unscrewing the tip and shaft.

13. A curette with a replaceable tip including:
    a tip with a proximal end that includes a threaded section and an outwardly extending elongated section with one or more flattened sides;
    a shaft with a proximal end and a distal mating end, the distal end including a threaded indent for receiving the proximal end of the tip, the indent being sized to contain epoxy;
    epoxy that hardens around the elongated section of the proximal end of the tip when the proximal end of the tip and the distal end of the shaft screw together to mate, the epoxy being softened to allow the threads of the tip and shaft to be unscrewed for tip replacement; and
    a handle with a distal end and a proximal end, the distal end being shaped to mate with the proximal end of the shaft.

14. The curette of claim 13 wherein the threads of the threaded sections of the tip and the shaft interlock when the proximal end of the tip and the distal end of the shaft screw together to mate.

15. The curette of claim 13 wherein
    the distal end of the handle includes a threaded section and an outwardly extending elongated section with one or more flattened sides, and
    the proximal end of the shaft includes a threaded indent that is shaped to receive the distal end of the handle, the indent being sized to contain epoxy that hardens around the elongated section of the distal end of the handle when the proximal end of the shaft and the distal end of the handle mate.

16. The curette of claim 14 wherein the tip has a distal end that is shaped for scraping.

17. The curette of claim 16 wherein the tip is coated with a durable coating from a proximal end to the threaded section.

18. The curette of claim 17 wherein the coating is titanium nitrate.

19. The curette of claim 16 wherein the distal end of the tip is shaped as one of a scoop or a ring.

20. A method for replacing a tip of a curette, the method including the steps of:

removing an attached tip by heating epoxy included in a threaded indent in a distal end of a shaft, the indent being sized to receive a threaded mating end of the tip, and unscrewing the tip from the indent;

partially filling the threaded indent in the distal end of the shaft with epoxy;

inserting the threaded mating end of a replacement tip in the partially-filled indent and screwing the shaft and tip together to interlock threads on the mating end of the replacement tip with the threads in the indent;

allowing the epoxy to harden around the mating end of the replacement tip, with one or more flattened sides of the replacement tip preventing relative rotation of the replacement tip; and attaching a handle to a proximal end of the shaft.

* * * * *